US012766145B2

(12) United States Patent
Kim et al.

(10) Patent No.: US 12,766,145 B2
(45) Date of Patent: Oct. 20, 2026

(54) PHARMACEUTICAL COMPOSITION COMPRISING UDENAFIL

(71) Applicant: COREPHARM BIO CO., LTD., Gyeonggi-do (KR)

(72) Inventors: Sang Wook Kim, Gyeonggi-do (KR); Hyun Tae Lim, Gyeonggi-do (KR); Young Lae Kim, Gyeonggi-do (KR); Jeong Tae Kim, Gyeonggi-do (KR)

(73) Assignee: COREPHARM BIO CO., LTD., Gyeonggi-do (KR)

( * ) Notice: Subject to any disclaimer, the term of this patent is extended or adjusted under 35 U.S.C. 154(b) by 773 days.

(21) Appl. No.: 17/627,722

(22) PCT Filed: Jul. 24, 2020

(86) PCT No.: PCT/KR2020/009800

§ 371 (c)(1),
(2) Date: Jan. 17, 2022

(87) PCT Pub. No.: WO2021/020820

PCT Pub. Date: Feb. 4, 2021

(65) Prior Publication Data

US 2022/0249493 A1 Aug. 11, 2022

(30) Foreign Application Priority Data

Jul. 26, 2019 (KR) ........................ 10-2019-0091056

(51) Int. Cl.

*A61K 31/519* (2006.01)
*A61K 9/00* (2006.01)
*A61K 47/12* (2006.01)
*A61K 47/40* (2006.01)

(52) U.S. Cl.

CPC .......... *A61K 31/519* (2013.01); *A61K 9/0095* (2013.01); *A61K 47/12* (2013.01); *A61K 47/40* (2013.01)

(58) Field of Classification Search

CPC .... A61K 31/519; A61K 9/0095; A61K 47/12; A61K 47/40
See application file for complete search history.

(56) References Cited

U.S. PATENT DOCUMENTS

2018/0325907 A1* 11/2018 Wang .................. A61K 31/575

FOREIGN PATENT DOCUMENTS

| | | | | | |
|---|---|---|---|---|---|
| CN | 102307597 | A | | 1/2012 | |
| JP | 2002-529467 | A | | 9/2002 | |
| JP | 2010-241798 | A | | 10/2010 | |
| KR | 10-2003-0042547 | A | | 6/2003 | |
| KR | 10-2004-0079012 | A | | 9/2004 | |
| KR | 10-0496372 | B1 | | 6/2005 | |
| KR | 10-2007-0100023 | A | | 10/2007 | |
| KR | 10-0792126 | B1 | | 1/2008 | |
| KR | 10-2017-0066334 | A | | 6/2017 | |
| TR | 201708240 | A2 | * | 10/2017 | A61K 31/519 |
| WO | WO-2011/030351 | A2 | | 3/2011 | |
| WO | WO-2013/062497 | A1 | | 5/2013 | |
| WO | WO-2016/025100 | A2 | | 2/2016 | |
| WO | WO-2016094567 | A1 | * | 6/2016 | A61K 31/197 |
| WO | WO-2017218894 | A1 | * | 12/2017 | A61K 9/0095 |
| WO | WO-2019/094989 | A1 | | 5/2019 | |
| WO | WO-2019/130052 | A1 | | 7/2019 | |

OTHER PUBLICATIONS

TR 201708240A English Translation (Year: 2017).*
Rychik, Circulation, 2019, 140, pp. 234-284, Originally Published Jul. 1, 2019 (Year: 2019).*
KR20030042547A English Translation (Year: 2003).*
KR20030042547 English Translation (Year: 2003).*
Coupland, Pharm. Res. Sep. 10, 2014; 31(11):2921-2939 (Year: 2014).*
Brewster et al.: "Cyclodextrins as pharmaceutical solubilizers", Advanced Drug Delivery Reviews, Elsevier, Amsterdam, NL, vol. 59 No. 7, Aug. 24, 2007, pp. 645-666.
Extended European Search Report from corresponding European Patent Application No. 20848224.0, dated Jul. 3, 2023.
International Search Report from corresponding PCT Application No. PCT/KR2020/009800, dated Nov. 2, 2020.

* cited by examiner

*Primary Examiner* — Andrew D Kosar
*Assistant Examiner* — Phillip Matthew Rzeczycki
(74) *Attorney, Agent, or Firm* — Harness, Dickey & Pierce, P.L.C.

(57) ABSTRACT

The present disclosure relates to a pharmaceutical composition comprising udenafil or a pharmaceutically acceptable salt thereof as an active ingredient, a pH adjusting agent, and cyclodextrin or a derivative thereof.

5 Claims, 1 Drawing Sheet

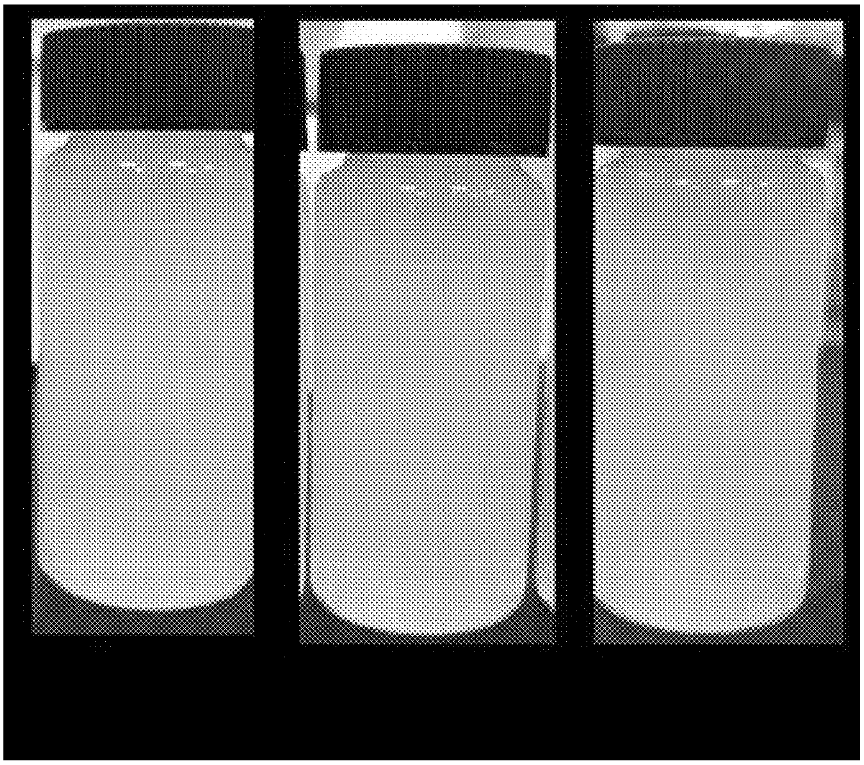

PHARMACEUTICAL COMPOSITION COMPRISING UDENAFIL

CROSS REFERENCE TO RELATED APPLICATION

This application is a national phase entry of PCT Application No. PCT/KR2020/009800, filed on Jul. 24, 2020, which claims the benefit of priority based on Korean Patent Application No. 10-2019-0091056, filed on Jul. 26, 2019, the entire disclosures of which are incorporated as a part of this specification.

TECHNICAL FIELD

The present invention relates to a pharmaceutical composition containing udenafil as an active ingredient.

BACKGROUND ART

Udenafil is a compound having the name 5-[2-propyloxy-5-(1-methyl-2-pyrrolidinyleneamidosulfonyl)phenyl]-1-methyl-1-propyl-1,6-dihydro-7H-pyrazolo(4,3-d)pyrimidin-7-one, is a phosphodiesterase type 5 inhibitor, and is a drug currently marketed for the treatment of erectile dysfunction. Udenafil has a structure of the following Formula:

[Formula]

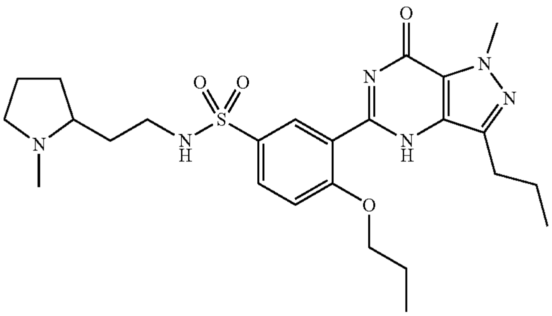

Korean Patent Nos. 10-0792126 and 10-0496372 disclose the use of udenafil for the treatment of pulmonary arterial hypertension, portal vein hypertension, and benign prostatic hyperplasia, and Korean Patent Application Publication No. 10-2017-0066334 discloses a method of improving myocardial performance in patients, who have had a Fontan procedure, using an udenafil composition.

The Fontan procedure is a palliative surgical procedure for a child born with a functional single ventricle congenital heart disease, and started as a procedure to connect the right atrium directly to the pulmonary artery in the case in which the right ventricle could not be used. This procedure was based on the discovery that, unlike the left ventricle, the right ventricle is not essential for maintaining pulmonary arterial blood flow. The Fontan procedure has been applied to patients with right ventricular hypoplasia, patients with tricuspid valve atresia, and single ventricle patients with only one ventricle. Recently, the surgical procedure has been significantly modified, and a technique of connecting the vena cava to the pulmonary arteries directly or through a conduit has been used.

A formulation of udenafil, which is currently used as a treatment for erectile dysfunction, is commercially available as a tablet formulation that is difficult to administer to patients with dysphagia and infants.

In the case of the Fontan patients mentioned above, the main age group for whom udenafil is used consists of children at the infant stage, it is preferable to formulate udenafil as a liquid or syrup rather than a tablet in order to improve the convenience of administration. However, when udenafil is formulated as a liquid or syrup, a problem arises in that the inherent strong bitter taste of udenafil or the numbing sensation caused by udenafil appears.

PRIOR ART DOCUMENTS

Patent Documents (Patent Document 1) Korean Patent No. 10-0792126
(Patent Document 2) Korean Patent No. 10-0496372
(Patent Document 3) Korean Patent Application Publication No. 10-2017-0066334

SUMMARY

Technical Problem

Accordingly, the present inventors have found that, when udenafil or a pharmaceutically acceptable salt thereof is formulated as a liquid or syrup, it is possible to improve the medication compliance of infant patients by masking the bitter taste and numbing sensation, thereby completing the present invention.

Therefore, an object of the present invention is to provide an oral liquid formulation (as defined in the Korean Pharmacopoeia 11th edition; for example, including liquid formulations, suspension formulations, lemonade formulations, etc.) or syrup formulation containing udenafil or a pharmaceutically acceptable salt thereof.

Another object of the present invention is to provide an oral liquid or syrup formulation containing udenafil or a pharmaceutically acceptable salt thereof, in which the active ingredient has improved uniformity.

Technical Solution

The present invention is directed to a pharmaceutical composition containing: udenafil or a pharmaceutically acceptable salt thereof; a pH adjusting agent; and cyclodextrin or a derivative thereof.

The composition of the present invention is intended for administration to patients, who have undergone a Fontan procedure, and is preferably in a liquid or syrup formulation which is convenient to administer to infant patients.

The composition of the present invention may further contain a viscosity modifier. In the present invention, the viscosity of the composition is preferably 400 to 4,000 cps. In addition, the pH of the composition of the present invention is preferably in the range of 3 to 6.

In the present invention, the cyclodextrin derivative may be at least one selected from the group consisting of α-cyclodextrin, β-cyclodextrin, γ-cyclodextrin, 2-hydroxypropyl-β-cyclodextrin, 2,6-dimethyl-β-cyclodextrin, sulfobutylether-7-β-cyclodextrin, 2-hydroxyethyl-β-cyclodextrin, (2-carboxymethoxy)propyl-β-cyclodextrin, 2-hydroxyethyl-γ-cyclodextrin, and 2-hydroxypropyl-γ-cyclodextrin.

In the present invention, the weight ratio between the udenafil or a pharmaceutically acceptable salt thereof and the cyclodextrin or a derivative thereof is preferably 1:0.1 to 10.

In the present invention, the viscosity modifier may be at least one selected from the group consisting of agar, xanthan gum, locust bean gum, guar gum, tragacanth gum, arabic gum, gellan gum, karaya gum, ghatti gum, tamarind gum, tara gum, acacia gum, chitosan, carrageenan, gelatin, pectin, alginic acid, sodium alginate, propylene glycol, hypromellose, hydroxyethyl cellulose, hydroxypropyl cellulose, hydroxyethyl methyl cellulose, polyethylene glycol, polyvinyl alcohol, povidone, and polyethylene oxide.

In the present invention, the pH adjusting agent may be at least one selected from the group consisting of citric acid, fumaric acid, succinic acid, adipic acid, aspartic acid, glutamic acid, maleic acid, lactic acid, tartaric acid, phosphoric acid, hydrochloric acid, and acetic acid.

Advantageous Effects

The pharmaceutical composition containing udenafil or a pharmaceutically acceptable salt thereof according to the present invention minimizes the inherent bitter taste of the drug and the numbing sensation caused by the drug, thereby improving the medication compliance of infant patients and dysphagia patients, who are main subjects. In addition, it is possible to provide a liquid or syrup composition containing udenafil, which does not undergo layer separation due to ensured uniformity of the liquid or syrup and has excellent quality due to good flowability.

BRIEF DESCRIPTION OF DRAWINGS

FIG. 1 is a photograph of the appearance of a composition according to an embodiment of the present invention, taken after a stability test.

DETAILED DESCRIPTION

Hereinafter, the present invention will be described in detail

Pharmaceutical Composition

The present invention is directed to a pharmaceutical composition containing: udenafil or a pharmaceutically acceptable thereof; a pH adjusting agent; and cyclodextrin or a derivative thereof.

As used herein, the term "pharmaceutically acceptable salt" means salts that are commonly used in the pharmaceutical industry. Examples of the salts include: inorganic ion salts formed with calcium, potassium, sodium, magnesium, etc.; inorganic acid salts formed with hydrochloric acid, nitric acid, phosphoric acid, bromic acid, iodic acid, perchloric acid, sulfuric acid, etc.; organic acid salts formed with acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts formed with methanesulfonic acid, ethanesulfonic acid, benzenesulfonic acid, p-toluenesulfonic acid, naphthalenesulfonic acid, etc.; amino acid salts formed with glycine, arginine, lysine, etc.; and amine salts formed with trimethylamine, triethylamine, ammonia, pyridine, picoline, etc. However, the types of salts meant in the present invention are not limited to the above listed salts.

The composition of the present invention relates to a pharmaceutical composition intended for administration to a patient who has undergone a Fontan procedure, and may treat or prevent conditions, symptoms and/or side effects related to a patient who has undergone a Fontan procedure, thereby, for example, improving cardiac output, or reducing pulmonary vascular resistance, or increasing exercise capacity, improving myocardial performance, or improving aerobic exercise performance.

In addition, the composition of the present invention relates to a pharmaceutical composition for the prevention or treatment of erectile dysfunction, and improves the medication compliance of erectile dysfunction patients (particularly, patients with difficulty in swallowing).

As used herein, the term "prevention" means delaying onset of a disease, disorder or disease. Prevention may be considered complete when onset of a disease, disorder or condition has been delayed for a predefined period of time.

As used herein, the term "treatment" refers to partially or completely alleviating, ameliorating, relieving, delaying onset of, inhibiting progression of, reducing severity of, or reducing incidence of one or more symptoms or features of a particular disease, disorder, and/or condition.

In one embodiment of the present invention, the pharmaceutical composition of the present invention may be may be prepared in a unit dose form or prepared to be contained in a multi-dose container by formulating the composition with a pharmaceutically acceptable carrier according to a method that a person skilled in the art can easily perform.

As used herein, the term "carrier" means a compound that facilitates the addition of the compound into a cell or tissue, and the term "pharmaceutically acceptable" refers to an additive which is physiologically acceptable and, when administered to the human beings, does not cause allergic reactions such as gastrointestinal disorders and dizziness, or similar reactions.

In one embodiment of the present invention, the pharmaceutically acceptable carrier is one that is commonly used in formulation, and examples thereof include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propylhydroxybenzoate, talc, magnesium stearate, and mineral oil. The pharmaceutical composition of the present invention may further contain, in addition to the above-described components, a lubricant, a wetting agent, a sweetener, a flavoring agent, an emulsifier, a suspending agent, a preservative, and the like.

In one embodiment of the present invention, the content of the additives in the pharmaceutical composition is not particularly limited and may be appropriately adjusted within the content range that is commonly used in formulation.

The composition of the present invention is preferably in the form of a liquid formulation or syrup formulation so that it may be conveniently administered orally to infant patients, who have undergone a Fontan procedure, according to the intended administration method.

As used herein, the term "administration" means providing a predetermined substance to a subject or patient in any suitable manner. Depending on the method as desired, the substance may be administered parenterally (for example, applied as an injectable formulation intravenously, subcutaneously, intraperitoneally or topically) or orally. Dosage may vary according to the patient's weight, age, sex, health condition and diet, the time of administration, the mode of administration, the rate of excretion, and the severity of the disease. The composition of the present invention is preferably administered orally.

As used herein, the term "oral administration" means that a substance prepared so that the active substance is digested is administered into the gastrointestinal tract for absorption. In order to formulate the pharmaceutical composition of the present invention into a form for oral administration, it is possible to use a binder such as lactose, saccharose, sorbitol, mannitol, starch, amylopectin, cellulose or gelatin; an excipient such as dicalcium phosphate; a disintegrant such as corn starch or sweet potato starch; and a lubricant such as magnesium stearate, calcium stearate, sodium stearyl fumarate or polyethylene glycol, and it is also possible to use a sweetener, fragrance, syrup or the like. Furthermore, for capsules, it is possible to additionally use a liquid carrier such as fatty oil, in addition to the above-mentioned substances.

A preferred dosage of the pharmaceutical composition of the present invention may vary depending on the patient's condition, weight, age, sex, health condition, diet, and constitution specificity, the nature of the formulation, the severity of the disease, the time, mode, duration or interval of administration of the composition, the excretion rate, and the form of drug, and may be appropriately selected by those skilled in the art. For example, the dosage may be in the range of about 0.1 to 10,000 mg/kg, but is not limited thereto, and may be administered once or several times a day.

The pharmaceutical composition of the present invention may include two separate formulations, or may consist of a single formulation, but is not limited thereto.

As used herein, the term "liquid formulation" refers to a liquid medicine for oral administration obtained by dissolving a pharmaceutical drug in water or an organic solvent. The liquid formulation has an advantage over a suspension or solid formulation in that drug absorption into the systemic circulation from the gastrointestinal tract is more effective. The liquid formulation may contain, in addition to, the pharmaceutical drug, an additional solute, and may also contain additives that give color, smell, sweetness or stability.

As used herein, the term "syrup" refers to a concentrated aqueous solution of sugar or a sugar substitute. In the present invention, the syrup is a formulation obtained by formulating a drug having an unpleasant taste, for example, a bitter taste, so that the drug is easy to take. The syrup is a formulation that is particularly suitable for children to take. In the present invention, the syrup may contain, in addition to purified water and extract, sugar or a sugar substituent that is used to give sweetness and viscosity, an antibacterial preservative, a sweetener, a flavoring agent, or a coloring agent, but is not limited thereto. Examples of a sweetener that may be contained in the syrup include, but are not limited to, sucrose, mannitol, sorbitol, xylitol, aspartame, stevioside, fructose, lactose, sucralose, saccharin, or menthol.

The composition of the present invention may further contain a viscosity modifier. In the present invention, the viscosity of the composition is preferably 400 to 4,000 cps, but is not limited thereto. In addition, the pH of the composition of the present invention is preferably in the range of 3 to 6, but is not limited thereto.

As used herein, the term "cps" means centipoise, which is a unit of viscosity.

As used herein, the term "cyclodextrin derivative" refers to a compound that may be derived from cyclodextrin, or a part of the compound.

In the present invention, the cyclodextrin derivative may be at least one selected from the group consisting of α-cyclodextrin, β-cyclodextrin, γ-cyclodextrin, 2-hydroxypropyl-β-cyclodextrin, 2,6-dimethyl-β-cyclodextrin, sulfobutylether-7-β-cyclodextrin, 2-hydroxyethyl-β-cyclodextrin, (2-carboxymethoxy)propyl-β-cyclodextrin, 2-hydroxyethyl-γ-cyclodextrin, and 2-hydroxypropyl-γ-cyclodextrin. Specifically, γ-cyclodextrin is preferably used alone or in combination with α-cyclodextrin.

In the present invention, the weight ratio between the udenafil or pharmaceutically acceptable salt thereof and the cyclodextrin or derivative thereof is preferably 1:0.1 to 10. Specifically, the weight ratio between the udenafil or pharmaceutically acceptable salt thereof and the cyclodextrin or derivative thereof is more preferably 1:1 to 5.

As used herein, the term "viscosity modifier" refers to a substance which is used to maintain the pharmaceutical composition at a stable state without layer separation by combining the liquid phase with the solid phase in the pharmaceutical composition and to increase the viscosity of the pharmaceutical composition.

In the present invention, the viscosity modifier may be at least one selected from the group consisting of agar, xanthan gum, locust bean gum, guar gum, tragacanth gum, arabic gum, gellan gum, karaya gum, ghatti gum, tamarind gum, tara gum, acacia gum, chitosan, carrageenan, gelatin, pectin, alginic acid, sodium alginate, propylene glycol, hypromellose, hydroxyethyl cellulose, hydroxypropyl cellulose, hydroxyethyl methyl cellulose, polyethylene glycol, polyvinyl alcohol, povidone, and polyethylene oxide, but is not limited thereto.

As used herein, the term "pH adjusting agent" refers to an excipient which is used to adjust the pH of the pharmaceutical composition to a desired value.

In the present invention, the pH adjusting agent may be at least one selected from the group consisting of citric acid, fumaric acid, succinic acid, adipic acid, aspartic acid, glutamic acid, maleic acid, lactic acid, tartaric acid, phosphoric acid, hydrochloric acid, and acetic acid, but is not limited thereto.

Method for Preventing or Treating Fontan Disease and Pulmonary Hypertension or Erectile Dysfunction Related to Fontan Disease The present invention provides a method for preventing or treating Fontan disease and pulmonary hypertension or erectile dysfunction related to Fontan disease, the method comprising a step of administering a therapeutically effective amount of the pharmaceutical composition to mammals including humans.

As used herein, the term "therapeutically effective amount" refers to an amount effective for preventing or treating Fontan disease and pulmonary hypertension or erectile dysfunction related to Fontan disease, for example, the amount of the pharmaceutical composition that is administered to the subject to be treated. The term may encompass an amount of the pharmaceutical composition that prevents the occurrence or recurrence of Fontan disease and pulmonary hypertension or erectile dysfunction related to Fontan disease, or alleviates a symptom of the disease, or diminishes any direct or indirect pathological consequences of the disease, or prevents metastasis of the disease, or decrease the rate of disease progression, or ameliorates or palliates the disease state, or achieves remission or improved prognosis. That is, the therapeutically effective amount may be interpreted as encompassing all doses at which Fontan disease and symptoms of pulmonary hypertension or erectile dysfunction related to Fontan disease are ameliorated or cured by the pharmaceutical composition.

The method for preventing or treating Fontan disease and pulmonary hypertension or erectile dysfunction related to Fontan disease also encompass inhibiting or averting symptoms of the disease as well as addressing the disease itself, prior to the onset of symptoms by administering the pharmaceutical composition. The magnitude of a prophylactic or therapeutic dose of a particular active ingredient in the management of a disease will vary depending on the nature and severity of the disease or condition, and the route by which the active ingredient is administered. The dose and the dose frequency will also vary according to the age, body weight, and response of the individual patient. Suitable dosing regimens can be readily selected by those skilled in the art with due consideration of such factors. In addition, the prevention or treatment method according to the present invention may further comprise administering a therapeutically effective amount of an additional active agent that is helpful in the prevention or treatment of Fontan disease and pulmonary hypertension or erectile dysfunction related to Fontan disease, together with the pharmaceutical composition. The additional active agent may exhibit a synergistic or additive effect with the pharmaceutical composition.

As used herein, the expression "mammals including humans" includes mammals such as humans, monkeys, cattle, horses, dogs, cats, rabbits, and rats.

Uses of Pharmaceutical Composition

The present invention provides the use of the pharmaceutical composition for use in the preparation of a formulation for Fontan disease and pulmonary hypertension or erectile dysfunction related to Fontan disease.

The present invention provides the use of the pharmaceutical composition for the treatment of Fontan disease and pulmonary hypertension or erectile dysfunction related to Fontan disease.

The pharmaceutical composition of the present invention for the preparation of a formulation for Fontan disease and pulmonary hypertension or erectile dysfunction related to Fontan disease may contain an acceptable carrier, and may further contain other agents.

Details mentioned above with respect to the pharmaceutical composition, prevention or treatment method and use according to the present invention are equally applied as long as they do not contradict each other.

Examples

Hereinafter, the present invention will be described in detail with reference to examples in order to help the understanding of the present invention. However, the following examples serve merely to illustrate the content of the present invention, and the scope of the present invention is not limited by the following examples. The embodiments of the present invention are provided to more completely explain the present invention to those of ordinary skill in the art.

Test Example 1: Udenafil Solubility Test at Different pHs

In order to evaluate the solubility of udenafil (free base) depending on pH, Preparation Examples 1 to 8 shown in Table 1 below were prepared and subjected to a solubility test. The results of the test are shown in Table 2 below.

TABLE 1

| Function | Component name | Prep. Ex. 1 | Prep. Ex. 2 | Prep. Ex. 3 | Prep. Ex. 4 | Prep. Ex. 5 | Prep. Ex. 6 | Prep. Ex. 7 | Prep. Ex. 8 |
|---|---|---|---|---|---|---|---|---|---|
| Active ingredient | Udenafil | 5 g | 5 g | 5 g | 5 g | 5 g | 5 g | 5 g | 5 g |
| pH adjusting | Citric acid | 27.5 mg | 45 mg | — | — | — | — | — | — |
| agent | Phosphoric acid (purity: 35%) | — | — | 0.05 ml | 0.3 ml | 0.5 ml | 0.7 ml | 1 ml | 1.5 ml |
| Solvent | Purified water | 5 ml | 5 ml | 5 ml | 5 ml | 5 ml | 5 ml | 5 ml | 5 ml |
| | pH | 6.83 | 6.67 | 6.54 | 6.10 | 5.76 | 3.19 | 1.87 | 1.36 |

Preparation Method for Preparation Examples 1 to 8

A pH adjusting agent was added to 5 ml of purified water, and the mixture was stirred for 10 minutes, and then udenafil was added thereto, thus preparing the solutions shown in Table 1 above. Each solution was stirred for 2 hours, and then a sample was taken therefrom, filtered using a 0.45 μm PVDF syringe filter, and subjected to a solubility test, and the pH was measured (pH measuring device: pH2700, EUTECH, USA).

HPLC analysis conditions
Detector: UV detector (292 nm)
Column: Aegispak C18-F 5 μm, 4.6×150 mm
Column temperature: 30° C.
Mobile phase: 2.72 g of $KH_2PO_4$ dissolved in 1 L of purified water (A); acetonitrile (B); A:B=700:300
Flow rate: 1.0 mL/min
Injection volume: 10 μL

TABLE 2

| | pH of solution | Solubility (mg/ml) |
|---|---|---|
| Preparation Example 1 | 6.83 | About 39.4 |
| Preparation Example 2 | 6.67 | About 60.0 |
| Preparation Example 3 | 6.54 | About 94.0 |
| Preparation Example 4 | 6.10 | About 426.6 |
| Preparation Example 5 | 5.76 | About 474.8 |
| Preparation Example 6 | 3.19 | About 467.5 |
| Preparation Example 7 | 1.87 | About 359.0 |
| Preparation Example 8 | 1.36 | About 347.5 |

Udenafil has a water solubility of about 0.12 mg/mL (Comparative Example 1) and is very poorly soluble in water, and it was confirmed in the above-described test that the solubility of udenafil changed depending on the pH of the solution. It was seen that the solubility was improved in Preparation Example 1 having a pH of 6.83, and the solubility greatly increased in Preparation Example 4 (pH 6.1) having a low pH. However, in Preparation Examples 7 and 8 in which the pH was lower than 2, the solubility was slightly lower than those in the Preparation Examples having a pH ranging from 3 to 6.

From these results, it can be confirmed that udenafil has the highest solubility in the range of pH 3 to 6.

Preparation of Comparative Examples 1 and 2

Using the components and contents shown in Table 3 below, a composition (Comparative Example 1) was prepared by adding udenafil added to purified water, and a composition (Comparative Example 2) was prepared by completely dissolving udenafil through pH adjustment with a pH adjusting agent.

TABLE 3

| Per 100 ml of composition | | Comparative | Comparative |
|---|---|---|---|
| Function | Component name | Example 1 | Example 2 |
| Active ingredient | Udenafil | 1,000 mg | 1,000 mg |
| pH adjusting agent | Citric acid | — | 180 mg |
| Solvent | Purified water | 100 ml | 100 ml |

Preparation method: each of the compositions shown in Table 3 was prepared according to the following preparation method.

Comparative Example 1 was prepared by adding udenafil to 100 ml of purified water, followed by stirring for 20 minutes.

Comparative Example 2 was prepared by adding a pH adjusting agent to 100 ml of purified water and adding udenafil to the solution, followed by stirring for 20 minutes.

Preparation of Comparative Examples 3 and 4

Udenafil syrup compositions (Comparative Examples 3 and 4) containing no cyclodextrin were prepared using the compositions shown in Table 4 below. Since the composition of Comparative Example 3 contained no pH adjusting agent, udenafil did not completely dissolve therein.

TABLE 4

| Per 100 ml of composition | | Comparative Example 3 | Comparative Example 4 |
|---|---|---|---|
| Function | Component name | mg/100 ml | mg/100 ml |
| Active ingredient | Udenafil | 1,000 | 1,000 |
| pH adjusting agent | Citric acid | — | 180 |
| Solvent | Purified water | 20 mL | 20 mL |
| Sweetener | Sucrose | 45,000 | 45,000 |
| Sweetener | Sucralose | 50 | 50 |
| Sweetener | Stevioside | 50 | 50 |
| Preservative | Methyl paraoxybenzoate | 30 | 30 |
| Preservative | Propyl paraoxybenzoate | 20 | 20 |
| Preservative | Sodium benzoate | 50 | 50 |
| Solvent | Purified water | q.s. | q.s. |

Preparation method: each of the compositions shown in Table 4 above was prepared according to the following preparation method.

(i) add a pH adjusting agent to 20 ml of purified water, followed by stirring for 10 minutes (however, this step is omitted in the preparation of Comparative Example 3 containing no pH adjusting agent).

(ii) add udenafil to the solution, followed by stirring for 20 minutes.

(iii) add sweeteners and preservatives to about 40 mL of separate purified water, and then dissolve them by stirring for 1 hour or more while heating at 90° C. or higher.

(iv) mix the solution, mixed in step (ii), with the solution prepared in step (iii), and then stir and cool the mixture, and then add purified water to the mixture to reach a final volume of 100 ml, thereby preparing each composition.

Preparation of Comparative Examples 5 to 15

Udenafil syrup compositions containing cyclodextrin were prepared using the compositions shown in Tables 5-1 and 5-2 below. Since the composition of Comparative Example 5 contained no pH adjusting agent, udenafil did not completely dissolve therein.

TABLE 5-1

| Per 100 ml of composition | | Comp. Example 5 | Comp. Example 6 | Comp. Example 7 | Comp. Example 8 | Comp. Example 9 | Comp. Example 10 |
|---|---|---|---|---|---|---|---|
| Function | Component name | mg/100 ml | mg/100 ml | mg/100 ml | mg/100 ml | mg/100 ml | mg/100 ml |
| Active ingredient | Udenafil | 1,000 | 1,000 | 1,000 | 1,000 | 1,000 | 1,000 |
| Excipient | α-cyclodextrin | — | — | 2,000 | 4,000 | 6,000 | — |
| Excipient | β-cyclodextrin | — | — | — | — | — | 2,000 |
| Excipient | γ-cyclodextrin | 4,000 | 4,000 | — | — | — | — |
| pH adjusting agent | Citric acid | — | 113 | 180 | 180 | 180 | 180 |
| Solvent | Purified water | 20 mL | 20 mL | 20 mL | 20 mL | 20 mL | 20 mL |
| Sweetener | Sucrose | 45,000 | 45,000 | 45,000 | 45,000 | 45,000 | 45,000 |
| Sweetener | Sucralose | 50 | 50 | 50 | 50 | 50 | 50 |
| Sweetener | Stevioside | 50 | 50 | 50 | 50 | 50 | 50 |
| Preservative | Methyl paraoxybenzoate | 30 | 30 | 30 | 30 | 30 | 30 |
| Preservative | Propyl paraoxybenzoate | 20 | 20 | 20 | 20 | 20 | 20 |
| Preservative | Sodium benzoate | 50 | 50 | 50 | 50 | 50 | 50 |
| Solvent | Purified water | q.s. | q.s. | q.s. | q.s. | q.s. | q.s. |

TABLE 5-2

| Per 100 ml of composition | | Comp. Example 11 | Comp. Example 12 | Comp. Example 13 | Comp. Example 14 | Comp. Example 15 |
|---|---|---|---|---|---|---|
| Function | Component name | mg/100 ml | mg/100 ml | mg/100 ml | mg/100 ml | mg/100 ml |
| Active ingredient | Udenafil | 1,000 | 1,000 | 1,000 | 1,000 | 1,000 |
| Excipient | α-cyclodextrin | — | — | — | — | — |
| Excipient | β-cyclodextrin | 4,000 | — | — | — | — |
| Excipient | γ-cyclodextrin | — | 2,000 | 4,000 | 6,000 | 8,000 |
| pH adjusting agent | Citric acid | 180 | 180 | 180 | 180 | 180 |
| Solvent | Purified water | 20 mL | 20 mL | 20 mL | 20 mL | 20 mL |
| Sweetener | Sucrose | 45,000 | 45,000 | 45,000 | 45,000 | 45,000 |
| Sweetener | Sucralose | 50 | 50 | 50 | 50 | 50 |
| Sweetener | Stevioside | 50 | 50 | 50 | 50 | 50 |
| Preservative | Methyl paraoxybenzoate | 30 | 30 | 30 | 30 | 30 |
| Preservative | Propyl paraoxybenzoate | 20 | 20 | 20 | 20 | 20 |
| Preservative | Sodium benzoate | 50 | 50 | 50 | 50 | 50 |
| Solvent | Purified water | q.s. | q.s. | q.s. | q.s. | q.s. |

Preparation method: each of the compositions shown in Table 5 above was prepared according to the following preparation method.

(i) add a pH adjusting agent to 20 ml of purified water, followed by stirring for 10 minutes (however, this step is omitted in the preparation of Comparative Example 5 containing no pH adjusting agent).

(ii) add udenafil to the solution, followed by stirring for 20 minutes.

(iii) adding cyclodextrin to the solution while heating to a temperature of 60° C., followed by stirring for 20 minutes.

(iv) add sweeteners and preservatives to about 40 mL of separate purified water, and then dissolve them by stirring for 1 hour or more while heating at 90° C. or higher.

(v) mix the solution, mixed in step (iii), with the solution prepared in step (iv), and then stir and cool the mixture, and then add purified water to the mixture to reach a final volume of 100 ml, thereby preparing each composition.

Preparation of Comparative Examples 16 to 23

Udenafil syrup compositions shown in Table 6 below, which contain cyclodextrin and a pH adjusting agent, were prepared.

TABLE 6

| Per 100 ml of composition | | Comp. Example 16 | Comp. Example 17 | Comp. Example 18 | Comp. Example 19 | Comp. Example 20 | Comp. Example 21 | Comp. Example 22 | Comp. Example 23 |
|---|---|---|---|---|---|---|---|---|---|
| Function | Component name | mg/100 ml | mg/100 ml | mg/100 ml | mg/100 ml | mg/100 ml | mg/100 ml | mg/100 ml | mg/100 ml |
| Active ingredient | Udenafil | 1,000 | 1,000 | 1,000 | 1,000 | 1,000 | 1,000 | 1,000 | 1,000 |
| Excipient | γ-cyclodextrin | 4,000 | 4,000 | 4,000 | 4,000 | 4,000 | 4,000 | 4,000 | 4,000 |
| pH adjusting agent | Citric acid | 180 | 180 | 180 | 180 | 180 | 180 | 180 | 180 |
| Solvent | Purified water | 20 mL | 20 mL | 20 mL | 20 mL | 20 mL | 20 mL | 20 mL | 20 mL |
| Sweetener | Sucrose | 45,000 | 45,000 | 45,000 | 45,000 | 45,000 | 45,000 | 45,000 | 45,000 |
| Sweetener | Sucralose | 50 | 50 | 50 | 50 | 50 | 50 | 50 | 50 |
| Sweetener | Stevioside | 50 | 50 | 50 | 50 | 50 | 50 | 50 | 50 |
| Viscosity modifier | Agar | 300 | — | — | 300 | 300 | 300 | 300 | 300 |
| Viscosity modifier | Hydroxypropyl cellulose | — | 100 | — | — | — | — | — | — |
| Viscosity modifier | Hydroxyethyl cellulose | — | — | 400 | 400 | 4,000 | 3,500 | 3,200 | 3,000 |
| Preservative | Methyl paraoxybenzoate | 30 | 30 | 30 | 30 | 30 | 30 | 30 | 30 |
| Preservative | Propyl paraoxybenzoate | 20 | 20 | 20 | 20 | 20 | 20 | 20 | 20 |
| Preservative | Sodium benzoate | 50 | 50 | 50 | 50 | 50 | 50 | 50 | 50 |
| Solvent | Purified water | q.s. | q.s. | q.s. | q.s. | q.s. | q.s. | q.s. | q.s. |

Preparation method: each of the compositions shown in Table 6 above was prepared according to the following preparation method.

(i) add a pH adjusting agent to 20 ml of purified water, followed by stirring for 10 minutes.

(ii) add udenafil to the solution, followed by stirring for 20 minutes.

(iii) add cyclodextrin to the solution while heating to a temperature of 60° C., followed by stirring for 20 minutes.

(iv) add sweeteners, viscosity modifiers and preservatives to about 40 mL of separate purified water, and then dissolve them by stirring for 1 hour or more while heating at 90° C. or higher.

(v) mix the solution, mixed in step (iii), with the solution prepared in step (iv), and then stir and cool the mixture, and then add purified water to the mixture to reach a final volume of 100 ml, thereby preparing each composition.

Preparation of Examples 1 to 20

The udenafil syrup compositions shown in Tables 7-1, 7-2 and 7-3 were prepared.

TABLE 7-1

| Per 100 ml of composition | | Example 1 | Example 2 | Example 3 | Example 4 | Example 5 | Example 6 |
|---|---|---|---|---|---|---|---|
| Function | Component name | mg/100 ml | mg/100 ml | mg/100 ml | mg/100 ml | mg/100 ml | mg/100 ml |
| Active ingredient | Udenafil | 1000 | 1000 | 1000 | 1000 | 1000 | 1000 |
| Excipient | α-cyclodextrin | — | — | — | — | — | — |
| Excipient | β-cyclodextrin | — | — | — | — | — | — |
| Excipient | γ-cyclodextrin | 4000 | 4000 | 4000 | 4000 | 4000 | 4000 |
| pH adjusting agent | Citric acid | 180 | 180 | 180 | 180 | 180 | 180 |
| pH adjusting agent | Hydrochloric acid (purity: 35 to 37%) | — | — | — | — | — | — |
| pH adjusting agent | Phosphoric acid (purity: 35%) | — | — | — | — | — | — |
| Solvent | Purified water | 20 mL | 20 mL | 20 mL | 20 mL | 20 mL | 20 mL |
| Sweetener | Sucrose | 45000 | 45000 | 45000 | 45000 | 45000 | 45000 |
| Sweetener | Sucralose | 50 | 50 | 50 | 50 | 50 | 50 |
| Sweetener | Stevioside | 50 | 50 | 50 | 50 | 50 | 50 |
| Viscosity modifier | Agar | — | — | — | — | 300 | 300 |
| Viscosity modifier | Hydroxypropyl cellulose | 250 | 500 | — | — | — | — |
| Viscosity modifier | Hydroxyethyl cellulose | — | — | 800 | 1200 | 800 | 1200 |
| Preservative | Methyl paraoxybenzoate | 30 | 30 | 30 | 30 | 30 | 30 |
| Preservative | Propyl paraoxybenzoate | 20 | 20 | 20 | 20 | 20 | 20 |
| Preservative | Sodium benzoate | 50 | 50 | 50 | 50 | 50 | 50 |
| Solvent | Purified water | q.s. | q.s. | q.s. | q.s. | q.s. | q.s. |

TABLE 7-2

| Per 100 ml of composition | | Example 7 | Example 8 | Example 9 | Example 10 | Example 11 | Example 12 | Example 13 |
|---|---|---|---|---|---|---|---|---|
| Function | Component name | mg/100 ml | mg/100 ml | mg/100 ml | mg/100 ml | mg/100 ml | mg/100 ml | mg/100 ml |
| Active ingredient | Udenafil | 1000 | 1000 | 1000 | 1000 | 1000 | 1000 | 1000 |
| Excipient | α-cyclodextrin | — | — | — | 1000 | 2000 | 1000 | 2000 |
| Excipient | β-cyclodextrin | — | — | — | — | — | — | — |
| Excipient | γ-cyclodextrin | 4000 | 4000 | 4000 | 1000 | 2000 | 2000 | 1000 |
| pH adjusting agent | Citric acid | 180 | 180 | 180 | 180 | 180 | 180 | 180 |
| pH adjusting agent | Hydrochloric acid (purity: 35 to 37%) | — | — | — | — | — | — | — |
| pH adjusting agent | Phosphoric acid (purity: 35%) | — | — | — | — | — | — | — |
| Solvent | Purified water | 20 mL | 20 mL | 20 mL | 20 mL | 20 mL | 20 mL | 20 mL |
| Sweetener | Sucrose | 45000 | 45000 | 45000 | 45000 | 45000 | 45000 | 45000 |
| Sweetener | Sucralose | 50 | 50 | 50 | 50 | 50 | 50 | 50 |
| Sweetener | Stevioside | 50 | 50 | 50 | 50 | 50 | 50 | 50 |
| Viscosity modifier | Agar | 300 | 300 | 300 | 300 | 300 | 300 | 300 |
| Viscosity modifier | Hydroxypropyl cellulose | — | — | — | — | — | — | — |

TABLE 7-2-continued

| Per 100 ml of composition | | Example 7 | Example 8 | Example 9 | Example 10 | Example 11 | Example 12 | Example 13 |
|---|---|---|---|---|---|---|---|---|
| Function | Component name | mg/100 ml | mg/100 ml | mg/100 ml | mg/100 ml | mg/100 ml | mg/100 ml | mg/100 ml |
| Viscosity modifier | Hydroxyethyl cellulose | 2000 | 2500 | 1600 | 1200 | 1200 | 1200 | 1200 |
| Preservative | Methyl paraoxybenzoate | 30 | 30 | 30 | 30 | 30 | 30 | 30 |
| Preservative | Propyl paraoxybenzoate | 20 | 20 | 20 | 20 | 20 | 20 | 20 |
| Preservative | Sodium benzoate | 50 | 50 | 50 | 50 | 50 | 50 | 50 |
| Solvent | Purified water | q.s. | q.s. | q.s. | q.s. | q.s. | q.s. | q.s. |

TABLE 7-3

| Per 100 ml of composition | | Example 14 | Example 15 | Example 16 | Example 17 | Example 18 | Example 19 | Example 20 |
|---|---|---|---|---|---|---|---|---|
| Function | Component name | mg/100 ml | mg/100 ml | mg/100 ml | mg/100 ml | mg/100 ml | mg/100 ml | mg/100 ml |
| Active ingredient | Udenafil | 1000 | 1000 | 1000 | 1000 | 1000 | 1000 | 1000 |
| Excipient | α-cyclodextrin | — | — | — | — | — | — | — |
| Excipient | β-cyclodextrin | — | — | — | — | — | — | — |
| Excipient | γ-cyclodextrin | 4000 | 4000 | 4000 | 4000 | 4000 | 4000 | 4000 |
| pH adjusting agent | Citric acid | 140 | 320 | — | — | — | — | 180 |
| pH adjusting agent | Hydrochloric acid | — | — | 0.2 mL | 0.12 mL | — | 0.3 mL | — |
| pH adjusting agent | Phosphoric acid | — | — | — | — | 0.2 mL | — | — |
| Solvent | Purified water | 20 mL | 20 mL | 20 mL | 20 mL | 20 mL | 20 mL | 20 mL |
| Sweetener | Sucrose | 45000 | 45000 | 45000 | 45000 | 45000 | 45000 | — |
| Sweetener | Sucralose | 50 | 50 | 50 | 50 | 50 | 50 | — |
| Sweetener | Stevioside | 50 | 50 | 50 | 50 | 50 | 50 | — |
| Viscosity modifier | Agar | 300 | 300 | 300 | 300 | 300 | 300 | 300 |
| Viscosity modifier | Hydroxypropyl cellulose | — | — | — | — | — | — | — |
| Viscosity modifier | Hydroxyethyl cellulose | 1200 | 1200 | 1200 | 1200 | 1200 | 1200 | 2400 |
| Preservative | Methyl paraoxybenzoate | 30 | 30 | 30 | 30 | 30 | 30 | 30 |
| Preservative | Propyl paraoxybenzoate | 20 | 20 | 20 | 20 | 20 | 20 | 20 |
| Preservative | Sodium benzoate | 50 | 50 | 50 | 50 | 50 | 50 | 50 |
| Solvent | Purified water | q.s. | q.s. | q.s. | q.s. | q.s. | q.s. | q.s. |

Preparation method: each of the compositions shown in Table 7 above was prepared according to the following preparation method.

(i) add pH adjusting agents to 20 ml of purified water, followed by stirring for 10 minutes (ii) add udenafil to the solution, followed by stirring for 20 minutes.

(iii) adding cyclodextrin to the solution while heating to a temperature of 60° C., followed by stirring for 20 minutes.

(iv) add sweeteners and preservatives to about 40 mL of separate purified water, and then dissolve them by stirring for 1 hour or more while heating at 90° C. or higher.

(v) mix the solution, mixed in step (iii), with the solution prepared in step (iv), and then stir and cool the mixture, and then add purified water to the mixture to reach a final volume of 100 ml, thereby preparing each composition.

Test Example 2: Flowability and Precipitation Degree Evaluation for Compositions The viscosity, pH value, relative flowability and precipitation degree of each of the compositions of the Comparative Examples and the Examples were measured, and the results were compared and shown in Table 8 below.

A. Viscosity Measurement

The viscosity of each composition was measured using a viscometer, and the results of the measurement are shown in Table 8 below.

Device used: LVDV-E, Brookfield, USA

Spindle: S62

Rotation speed: 30 rpm

B. pH Measurement

The pH of each composition was measured using a viscometer, and the results of the measurement are shown in Table 8 below.

Device used: pH2700, EUTECH, USA

C. Comparison of Flowability

In order to compare relative flowability, 1 ml of each sample was allowed to flow along a ramp under the following conditions, and the time taken to reach the bottom was compared between the samples, and the results are shown in Table 8 below.

Ramp material: polypropylene

Ramp angle: 45°

Ramp length: 10 cm

D. Evaluation of Layer Separation

In order to evaluate layer separation, each sample was left to stand at room temperature for 1 month, and then whether layer separation would occur was determined by visual observation. The results are shown in Table 8 below.

TABLE 8

| | pH | Viscosity (cps) | Layer separation | Flowability |
|---|---|---|---|---|
| Comparative Example 3 | 7.6 | 33 | ○ | 1 sec |
| Comparative Example 4 | 5.3 | 31 | ○ | 1 sec |
| Comparative Example 5 | 7.6 | 34 | ○ | 1 sec |
| Comparative Example 6 | 6.6 | 33 | ○ | 1 sec |
| Comparative Example 7 | 5.3 | 33 | ○ | 1 sec |
| Comparative Example 8 | 5.3 | 35 | ○ | 1 sec |
| Comparative Example 9 | 5.3 | 37 | ○ | 1 sec |
| Comparative Example 10 | 5.3 | 31 | ○ | 1 sec |
| Comparative Example 11 | 5.3 | 35 | ○ | 1 sec |
| Comparative Example 12 | 5.3 | 33 | ○ | 1 sec |
| Comparative Example 13 | 5.3 | 33 | ○ | 1 sec |
| Comparative Example 14 | 5.4 | 35 | ○ | 1 sec |
| Comparative Example 15 | 5.4 | 31 | ○ | 1 sec |
| Comparative Example 16 | 5.2 | 297 | ○ | 2 sec |
| Comparative Example 17 | 5.3 | 191 | ○ | 2 sec |
| Comparative Example 18 | 5.3 | 65 | ○ | 1 sec |
| Comparative Example 19 | 5.3 | 131 | ○ | 2 sec |
| Comparative Example 20 | 5.3 | 38690 | X | Almost no flow |
| Comparative Example 21 | 5.3 | 13080 | X | Almost no flow |
| Comparative Example 22 | 5.3 | 9840 | X | 3 min and 40 sec |
| Comparative Example 23 | 5.3 | 5210 | X | 1 min and 40 sec |
| Example 1 | 5.3 | 689 | X | 5 sec |
| Example 2 | 5.3 | 1196 | X | 12 sec |
| Example 3 | 5.3 | 431 | X | 3 sec |
| Example 4 | 5.3 | 849 | X | 7 sec |
| Example 5 | 5.3 | 420 | X | 3 sec |
| Example 6 | 5.3 | 890 | X | 6 sec |
| Example 7 | 5.3 | 2714 | X | 55 sec |
| Example 8 | 5.3 | 3310 | X | 1 min and 10 sec |
| Example 9 | 5.3 | 1221 | X | 15 sec |
| Example 10 | 5.3 | 831 | X | 7 sec |
| Example 11 | 5.3 | 894 | X | 7 sec |
| Example 12 | 5.3 | 811 | X | 6 sec |
| Example 13 | 5.3 | 856 | X | 6 sec |
| Example 14 | 6.03 | 842 | X | 6 sec |
| Example 15 | 4.07 | 887 | X | 6 sec |
| Example 16 | 3.06 | 854 | X | 6 sec |
| Example 17 | 4.85 | 857 | X | 6 sec |
| Example 18 | 2.14 | 813 | X | 6 sec |
| Example 19 | 2 | 854 | X | 6 sec |
| Example 20 | 5.2 | 738 | X | 5 sec |

As a result of examining the viscosity, pH, flowability, and degree of layer separation for each sample, it was confirmed that layer separation was observed in Comparative Examples 3 to 19 having a viscosity of 297 cps or less, indicating that the stability of the solution in each of Comparative Examples 3 to 19 was not good.

It was confirmed that the sample having a viscosity of 431 cps or more was stable without layer separation. However, it was confirmed that, in the case of Comparative Examples 20 to 21 having a viscosity of 13000 cps or more, the syrup hardly flowed even on the ramp. It was confirmed that the compositions of Comparative Examples 22 and 23 having a viscosity of 5210 cps or more flowed, but the times taken to reach the bottom were 1 min and 40 sec and 3 min and 40 sec, respectively, suggesting that these compositions had very poor flowability. If a liquid or syrup formulation having poor flowability as described above, inconvenience may cause when the liquid or syrup formulation is taken in small portions, and the dosage may not be constant, suggesting that the liquid or syrup formulation is not suitable.

Test Example 3: Sensory Evaluation

A sensory test for bitter taste and numbing sensation for each composition was performed on 10 healthy adults. The results of the test were evaluated according to the evaluation criteria shown in Table 9 below, and the average values of 10 people are shown in Tables 10 and 11 below.

TABLE 9

| Score | Bitter taste | Numbing sensation |
|---|---|---|
| 0 | No bitter taste | No numbing sensation |
| 1 | Slight bitter taste that is almost indistinguishable | Slight numbing sensation that is almost indistinguishable |
| 2 | A little bitter taste | A little numbing sensation |
| 3 | Moderately bitter | Moderately numbing |
| 4 | Strong and repulsive bitter taste | Strong and repulsive numbing sensation |
| 5 | Very strong bitter taste | Very strong numbing sensation |

TABLE 10

| No. | 1 | 2 | 3 | 4 | 5 | 6 | 7 | 8 | 9 | 10 | Average |
|---|---|---|---|---|---|---|---|---|---|---|---|
| Comp. Example 1 | 5 | 5 | 5 | 5 | 5 | 5 | 5 | 5 | 5 | 5 | 5 |
| Comp. Example 2 | 5 | 5 | 5 | 5 | 5 | 5 | 5 | 5 | 5 | 5 | 5 |
| Comp. Example 3 | 3 | 3 | 4 | 4 | 4 | 3 | 3 | 4 | 3 | 4 | 3.5 |
| Comp. Example 4 | 3 | 3 | 3 | 4 | 3 | 4 | 3 | 4 | 3 | 3 | 3.3 |
| Comp. Example 5 | 3 | 3 | 4 | 3 | 4 | 3 | 4 | 3 | 3 | 3 | 3.3 |
| Comp. Example 6 | 3 | 3 | 4 | 3 | 4 | 3 | 4 | 3 | 4 | 3 | 3.4 |
| Comp. Example 7 | 3 | 3 | 2 | 2 | 3 | 3 | 3 | 2 | 3 | 2 | 2.6 |
| Comp. Example 8 | 3 | 2 | 3 | 2 | 2 | 2 | 2 | 3 | 2 | 2 | 2.3 |
| Comp. Example 9 | 2 | 2 | 2 | 2 | 2 | 2 | 2 | 2 | 3 | 2 | 2.1 |
| Comp. Example 10 | 3 | 3 | 3 | 3 | 2 | 3 | 3 | 3 | 2 | 3 | 2.8 |
| Comp. Example 11 | 3 | 3 | 2 | 3 | 2 | 3 | 2 | 3 | 2 | 3 | 2.6 |
| Comp. Example 12 | 3 | 2 | 3 | 2 | 3 | 2 | 2 | 3 | 2 | 3 | 2.5 |
| Comp. Example 13 | 2 | 2 | 2 | 2 | 2 | 2 | 3 | 2 | 2 | 2 | 2.1 |
| Comp. Example 14 | 2 | 2 | 2 | 3 | 2 | 2 | 2 | 2 | 2 | 2 | 2.1 |
| Comp. Example 15 | 2 | 2 | 2 | 2 | 2 | 3 | 2 | 2 | 3 | 2 | 2.2 |
| Comp. Example 16 | 2 | 2 | 3 | 2 | 2 | 3 | 2 | 2 | 2 | 2 | 2.2 |
| Comp. Example 17 | 2 | 3 | 3 | 2 | 3 | 2 | 2 | 2 | 2 | 2 | 2.3 |
| Comp. Example 18 | 2 | 2 | 2 | 3 | 2 | 3 | 2 | 2 | 2 | 3 | 2.3 |
| Comp. Example 19 | 2 | 2 | 3 | 2 | 2 | 2 | 2 | 3 | 2 | 2 | 2.2 |
| Comp. Example 20 | 3 | 2 | 3 | 2 | 2 | 3 | 3 | 2 | 2 | 3 | 2.5 |

TABLE 10-continued

| No. | 1 | 2 | 3 | 4 | 5 | 6 | 7 | 8 | 9 | 10 | Average |
|---|---|---|---|---|---|---|---|---|---|---|---|
| Comp. Example 21 | 3 | 2 | 3 | 3 | 2 | 2 | 3 | 3 | 2 | 3 | 2.6 |
| Comp. Example 22 | 2 | 3 | 3 | 2 | 2 | 3 | 2 | 3 | 2 | 2 | 2.4 |
| Comp. Example 23 | 2 | 2 | 3 | 2 | 2 | 3 | 3 | 2 | 2 | 2 | 2.3 |
| Example 1 | 2 | 3 | 2 | 2 | 2 | 2 | 3 | 2 | 3 | 2 | 2.3 |
| Example 2 | 3 | 2 | 2 | 2 | 2 | 3 | 2 | 2 | 2 | 3 | 2.3 |
| Example 3 | 2 | 2 | 3 | 2 | 2 | 2 | 2 | 2 | 2 | 2 | 2.1 |
| Example 4 | 2 | 2 | 3 | 2 | 2 | 2 | 3 | 2 | 2 | 2 | 2.2 |
| Example 5 | 3 | 2 | 2 | 2 | 3 | 2 | 2 | 2 | 3 | 2 | 2.3 |
| Example 6 | 3 | 2 | 2 | 2 | 2 | 2 | 2 | 3 | 2 | 2 | 2.2 |
| Example 7 | 3 | 2 | 2 | 3 | 2 | 2 | 3 | 2 | 2 | 2 | 2.3 |
| Example 8 | 2 | 2 | 3 | 2 | 2 | 3 | 2 | 2 | 2 | 2 | 2.2 |
| Example 9 | 2 | 3 | 2 | 2 | 2 | 3 | 2 | 3 | 2 | 2 | 2.3 |
| Example 10 | 3 | 3 | 2 | 3 | 3 | 3 | 2 | 3 | 3 | 3 | 2.8 |
| Example 11 | 2 | 2 | 3 | 3 | 2 | 3 | 2 | 2 | 3 | 2 | 2.4 |
| Example 12 | 2 | 3 | 2 | 2 | 2 | 2 | 3 | 2 | 2 | 3 | 2.3 |
| Example 13 | 2 | 3 | 2 | 3 | 2 | 2 | 2 | 2 | 3 | 2 | 2.3 |
| Example 14 | 2 | 3 | 2 | 2 | 3 | 2 | 2 | 2 | 2 | 3 | 2.3 |
| Example 15 | 2 | 2 | 2 | 3 | 2 | 2 | 3 | 2 | 2 | 2 | 2.2 |
| Example 16 | 2 | 2 | 3 | 2 | 3 | 2 | 2 | 2 | 2 | 2 | 2.2 |
| Example 17 | 2 | 2 | 2 | 2 | 2 | 2 | 2 | 2 | 3 | 2 | 2.1 |
| Example 18 | 2 | 3 | 2 | 2 | 3 | 2 | 2 | 2 | 2 | 3 | 2.3 |
| Example 19 | 2 | 2 | 3 | 2 | 2 | 3 | 2 | 2 | 2 | 2 | 2.2 |
| Example 20 | 4 | 2 | 3 | 2 | 3 | 4 | 2 | 3 | 3 | 2 | 2.8 |

TABLE 11

| No. | 1 | 2 | 3 | 4 | 5 | 6 | 7 | 8 | 9 | 10 | Average |
|---|---|---|---|---|---|---|---|---|---|---|---|
| Comp. Example 1 | 5 | 5 | 5 | 5 | 5 | 5 | 5 | 5 | 5 | 5 | 5 |
| Comp. Example 2 | 5 | 5 | 5 | 5 | 5 | 5 | 5 | 5 | 5 | 5 | 5 |
| Comp. Example 3 | 5 | 5 | 5 | 5 | 5 | 4 | 5 | 5 | 4 | 5 | 4.8 |
| Comp. Example 4 | 5 | 4 | 5 | 5 | 4 | 5 | 5 | 5 | 5 | 5 | 4.8 |
| Comp. Example 5 | 5 | 5 | 5 | 5 | 4 | 5 | 5 | 5 | 5 | 5 | 4.9 |
| Comp. Example 6 | 5 | 5 | 4 | 5 | 5 | 5 | 4 | 5 | 4 | 5 | 4.7 |
| Comp. Example 7 | 1 | 2 | 2 | 1 | 2 | 2 | 2 | 1 | 2 | 2 | 1.7 |
| Comp. Example 8 | 1 | 1 | 0 | 1 | 1 | 0 | 1 | 1 | 0 | 1 | 0.7 |
| Comp. Example 9 | 1 | 0 | 1 | 0 | 0 | 0 | 1 | 1 | 1 | 1 | 0.6 |
| Comp. Example 10 | 1 | 2 | 1 | 2 | 2 | 2 | 2 | 2 | 2 | 2 | 1.8 |
| Comp. Example 11 | 1 | 2 | 1 | 2 | 2 | 2 | 1 | 2 | 2 | 2 | 1.7 |
| Comp. Example 12 | 2 | 1 | 2 | 1 | 1 | 2 | 2 | 1 | 2 | 1 | 1.5 |
| Comp. Example 13 | 0 | 1 | 0 | 1 | 0 | 0 | 1 | 1 | 0 | 1 | 0.5 |
| Comp. Example 14 | 1 | 1 | 0 | 1 | 0 | 1 | 0 | 1 | 0 | 1 | 0.6 |
| Comp. Example 15 | 1 | 0 | 0 | 1 | 1 | 0 | 1 | 1 | 0 | 0 | 0.5 |
| Comp. Example 16 | 1 | 1 | 0 | 1 | 0 | 1 | 1 | 0 | 1 | 1 | 0.7 |
| Comp. Example 17 | 1 | 0 | 1 | 1 | 0 | 1 | 1 | 0 | 1 | 0 | 0.6 |
| Comp. Example 18 | 1 | 0 | 1 | 1 | 0 | 0 | 1 | 0 | 1 | 1 | 0.6 |
| Comp. Example 19 | 0 | 0 | 1 | 0 | 1 | 1 | 0 | 1 | 1 | 0 | 0.5 |
| Comp. Example 20 | 1 | 0 | 1 | 1 | 0 | 1 | 0 | 1 | 1 | 1 | 0.7 |
| Comp. Example 21 | 1 | 0 | 1 | 1 | 1 | 0 | 1 | 1 | 1 | 1 | 0.8 |
| Comp. Example 22 | 1 | 1 | 0 | 1 | 0 | 1 | 1 | 0 | 1 | 1 | 0.7 |

TABLE 11-continued

| No. | 1 | 2 | 3 | 4 | 5 | 6 | 7 | 8 | 9 | 10 | Average |
|---|---|---|---|---|---|---|---|---|---|---|---|
| Comp. Example 23 | 1 | 0 | 1 | 1 | 0 | 1 | 0 | 1 | 1 | 0 | 0.6 |
| Example 1 | 1 | 1 | 0 | 1 | 1 | 0 | 0 | 1 | 0 | 1 | 0.6 |
| Example 2 | 0 | 0 | 1 | 1 | 1 | 0 | 1 | 1 | 0 | 0 | 0.5 |
| Example 3 | 1 | 0 | 0 | 1 | 1 | 1 | 0 | 1 | 0 | 0 | 0.5 |
| Example 4 | 0 | 0 | 0 | 1 | 1 | 0 | 1 | 0 | 1 | 0 | 0.4 |
| Example 5 | 0 | 0 | 1 | 0 | 1 | 0 | 0 | 1 | 1 | 0 | 0.4 |
| Example 6 | 0 | 1 | 0 | 1 | 1 | 1 | 0 | 1 | 0 | 1 | 0.6 |
| Example 7 | 1 | 0 | 1 | 0 | 1 | 1 | 0 | 1 | 1 | 0 | 0.6 |
| Example 8 | 1 | 0 | 1 | 1 | 0 | 1 | 0 | 1 | 1 | 0 | 0.6 |
| Example 9 | 0 | 0 | 1 | 1 | 0 | 1 | 1 | 0 | 1 | 0 | 0.5 |
| Example 10 | 0 | 1 | 2 | 1 | 1 | 2 | 1 | 2 | 1 | 2 | 1.3 |
| Example 11 | 0 | 1 | 0 | 1 | 0 | 1 | 1 | 0 | 1 | 0 | 0.5 |
| Example 12 | 1 | 0 | 1 | 1 | 0 | 1 | 0 | 1 | 1 | 0 | 0.6 |
| Example 13 | 0 | 1 | 0 | 1 | 0 | 1 | 1 | 0 | 1 | 1 | 0.6 |
| Example 14 | 1 | 1 | 1 | 0 | 1 | 1 | 0 | 0 | 1 | 0 | 0.6 |
| Example 15 | 1 | 0 | 1 | 0 | 1 | 0 | 1 | 0 | 1 | 0 | 0.5 |
| Example 16 | 0 | 1 | 1 | 1 | 0 | 0 | 1 | 1 | 0 | 1 | 0.6 |
| Example 17 | 1 | 1 | 0 | 1 | 1 | 1 | 1 | 0 | 1 | 0 | 0.7 |
| Example 18 | 1 | 0 | 0 | 1 | 1 | 0 | 1 | 1 | 1 | 1 | 0.7 |
| Example 19 | 1 | 0 | 1 | 1 | 0 | 0 | 1 | 1 | 0 | 1 | 0.6 |
| Example 20 | 1 | 0 | 1 | 0 | 1 | 1 | 1 | 0 | 1 | 1 | 0.7 |

As a result of sensory evaluation, Comparative Example 1 containing udenafil dispersed in purified water and Comparative Example 2 containing udenafil completely dissolved by pH adjustment all showed a strong bitter taste and numbing sensation.

Comparative Examples 3 and 4 prepared as the syrup formulations had a slightly decreased bitter taste, but the numbing sensation caused thereby did not significantly differ from that caused by Comparative Examples 1 and 2.

The compositions of Comparative Examples 5 and 6 contained γ-cyclodextrin, but the evaluation values of bitter taste and numbing sensation thereof did not significantly differ from those of Comparative Examples 2 and 3 due to the udenafil particles dispersed without being completely dissolved.

It was confirmed that, in the case of the compositions of the remaining Comparative Examples and Examples, due to the addition of the cyclodextrins, the bitter taste and numbing sensation decreased, and in particular, the numbing sensation significantly decreased.

The test results were comprehensively evaluated according to the criteria shown in Table 12 below, and the results of the evaluation results are shown in Table 13 below.

TABLE 12

| | Layer separation | Flowability | Bitter taste | Numbing sensation |
|---|---|---|---|---|
| Criteria for suitability | No layer separation | Within 1 min and 30 sec | Score of 3 or less | Score of 3 or less |

TABLE 13

| | Layer separation | Flowability | Bitter taste | Numbing sensation |
|---|---|---|---|---|
| Comparative Example 1 | — | — | Unsuitable | Unsuitable |
| Comparative Example 2 | — | — | Unsuitable | Unsuitable |
| Comparative Example 3 | Unsuitable | Suitable | Unsuitable | Unsuitable |
| Comparative Example 4 | Unsuitable | Suitable | Unsuitable | Unsuitable |
| Comparative Example 5 | Unsuitable | Suitable | Unsuitable | Unsuitable |
| Comparative Example 6 | Unsuitable | Suitable | Unsuitable | Unsuitable |
| Comparative Example 7 | Unsuitable | Suitable | Suitable | Suitable |
| Comparative Example 8 | Unsuitable | Suitable | Suitable | Suitable |

TABLE 13-continued

| | Layer separation | Flow-ability | Bitter taste | Numbing sensation |
|---|---|---|---|---|
| Comparative Example 9 | Unsuitable | Suitable | Suitable | Suitable |
| Comparative Example 10 | Unsuitable | Suitable | Suitable | Suitable |
| Comparative Example 11 | Unsuitable | Suitable | Suitable | Suitable |
| Comparative Example 12 | Unsuitable | Suitable | Suitable | Suitable |
| Comparative Example 13 | Unsuitable | Suitable | Suitable | Suitable |
| Comparative Example 14 | Unsuitable | Suitable | Suitable | Suitable |
| Comparative Example 15 | Unsuitable | Suitable | Suitable | Suitable |
| Comparative Example 16 | Unsuitable | Suitable | Suitable | Suitable |
| Comparative Example 17 | Unsuitable | Suitable | Suitable | Suitable |
| Comparative Example 18 | Unsuitable | Suitable | Suitable | Suitable |
| Comparative Example 19 | Unsuitable | Suitable | Suitable | Suitable |
| Comparative Example 20 | Suitable | Unsuitable | Suitable | Suitable |
| Comparative Example 21 | Suitable | Unsuitable | Suitable | Suitable |
| Comparative Example 22 | Suitable | Unsuitable | Suitable | Suitable |
| Comparative Example 23 | Suitable | Unsuitable | Suitable | Suitable |
| Example 1 | Suitable | Suitable | Suitable | Suitable |
| Example 2 | Suitable | Suitable | Suitable | Suitable |
| Example 3 | Suitable | Suitable | Suitable | Suitable |
| Example 4 | Suitable | Suitable | Suitable | Suitable |
| Example 5 | Suitable | Suitable | Suitable | Suitable |
| Example 6 | Suitable | Suitable | Suitable | Suitable |
| Example 7 | Suitable | Suitable | Suitable | Suitable |
| Example 8 | Suitable | Suitable | Suitable | Suitable |
| Example 9 | Suitable | Suitable | Suitable | Suitable |
| Example 10 | Suitable | Suitable | Suitable | Suitable |
| Example 11 | Suitable | Suitable | Suitable | Suitable |
| Example 12 | Suitable | Suitable | Suitable | Suitable |
| Example 13 | Suitable | Suitable | Suitable | Suitable |
| Example 14 | Suitable | Suitable | Suitable | Suitable |
| Example 15 | Suitable | Suitable | Suitable | Suitable |
| Example 16 | Suitable | Suitable | Suitable | Suitable |
| Example 17 | Suitable | Suitable | Suitable | Suitable |
| Example 18 | Suitable | Suitable | Suitable | Suitable |
| Example 19 | Suitable | Suitable | Suitable | Suitable |
| Example 20 | Suitable | Suitable | Suitable | Suitable |

From the above results, it was confirmed that, the viscosity of the composition was 400 cps or more, no layer separation appeared, but when the viscosity of the composition was excessively high, the flowability thereof was very low, which causes difficulties in commercialization, suggesting that a suitable viscosity range is 400 to 4,000 cps.

As a result of sensory evaluation, it was confirmed that the bitter taste and the numbing sensation significantly decreased in the compositions containing the cyclodextrins, but when udenafil was not dissolved due to a high pH of the composition, the bitter taste and the numbing sensation hardly decreased even when the cyclodextrins were used. Therefore, the most suitable pH of the composition is in the range of pH 3 to 6, at which the solubility of udenafil is the highest.

The compositions of Examples 1 to 20, which satisfied these criteria, showed satisfactory results in all items, including layer separation, flowability, bitter taste and numbing sensation, compared to the compositions of Comparative Examples 1 to 23.

Test Example 4: Stability Test for Composition

In the above results, Example 6, which showed all suitable results, was selected. In order to evaluate the stability thereof, Example 6 was evaluated for its appearance (layer separation), content, impurities, pH and viscosity under stress conditions (60° C.) and accelerated conditions (40° C. and 75% RH). The test results are shown in Table 14 below and FIG. 1.

A. Appearance

Visual observation was performed.

B. Content and Impurities

Udenafil concentration of syrup composition: 10 mg/ml

Sample preparation: 20 mg of the syrup composition as udenafil was taken and placed in a 100-ml-volume flask, 80% of which was then filled with a diluent, followed by stirring for 1 hour. Then, the solution was diluted to the volume mark with a diluent, and then filtered through a 0.45-μm PVDF syringe filter, and the filtrate was used as a test sample.

HPLC analysis conditions

Detector: UV detector (292 nm)

Column: Aegispak C18-F 5 μm, 4.6×150 mm

Column temperature: 30° C.

Mobile Phase:

2.72 g $KH_2PO_4$ dissolved in 1 L of purified water (A); acetonitrile (B); A:B=700:300

Flow rate: 1.0 mL/min

Injection volume: 10 μL

C. pH Measurement pH was measured using a pH meter.

Device used: pH2700, EUTECH, USA

D. Viscosity Measurement

Viscosity was measured using a viscometer.

Device used: LVDV-E, Brookfield, USA

Spindle: S62

Rotation speed: 30 rpm

TABLE 14

| Test items | Criteria | Initial | Stress for 4 weeks | Accelerated for 1 month |
|---|---|---|---|---|
| Appearance (layer separation) | Uniform without layer separation | Suitable | Suitable | Suitable |
| Content | 95 to 105% | 100.4 ± 0.1 | 100.9 ± 1.1 | 100.9 ± 1.0 |
| Impurities | Total impurity content of 2.0% or less | 0.11 | 0.13 | 0.14 |
| pH | 3 to 6 | 5.15 | 4.98 | 5.12 |
| Viscosity | 400 to 4,000 cps | 864 | 920 | 867 |

As a result of the stability test, the composition of the Examples showed suitable results in all items, including appearance, content, impurities, pH and viscosity.

INDUSTRIAL APPLICABILITY

The pharmaceutical composition containing udenafil or a pharmaceutically acceptable salt thereof according to the present invention minimizes the inherent bitter taste of the drug and the numbing sensation caused by the drug, thereby improving the medication compliance of infant patients who are main subjects. In addition, it is possible to provide a liquid or syrup composition containing udenafil, which does not undergo layer separation due to ensured uniformity of the liquid or syrup and has excellent quality due to good flowability.

What is claimed is:

1. A pharmaceutical composition comprising: udenafil or a pharmaceutically acceptable salt thereof; a pH adjusting agent; a viscosity modifier; and cyclodextrin or a derivative thereof;

wherein the pharmaceutical composition is a liquid or syrup formulation for oral administration;

wherein the pharmaceutical composition has a viscosity of 400 to 4,000 cps, wherein the pharmaceutical composition has a pH ranging from 3 to 6, and wherein a weight ratio between the udenafil or pharmaceutically acceptable salt thereof and the cyclodextrin or derivative thereof is 1:1 to 5.

2. The pharmaceutical composition of claim 1, wherein the cyclodextrin derivative is at least one selected from the group consisting of α-cyclodextrin, β-cyclodextrin, γ-cyclodextrin, 2-hydroxypropyl-β-cyclodextrin, 2,6-dimethyl-β-cyclodextrin, sulfobutylether-7-β-cyclodextrin, 2-hydroxyethyl-β-cyclodextrin, (2-carboxymethoxy) propyl-β-cyclodextrin, 2-hydroxyethyl-γ-cyclodextrin, and 2-hydroxypropyl-γ-cyclodextrin.

3. The pharmaceutical composition of claim 1, wherein the viscosity modifier is at least one selected from the group consisting of agar, xanthan gum, locust bean gum, guar gum, tragacanth gum, arabic gum, gellan gum, karaya gum, ghatti gum, tamarind gum, tara gum, acacia gum, chitosan, carrageenan, gelatin, pectin, alginic acid, sodium alginate, propylene glycol, hypromellose, hydroxyethyl cellulose, hydroxypropyl cellulose, hydroxyethyl methyl cellulose, polyethylene glycol, polyvinyl alcohol, povidone, and polyethylene oxide.

4. The pharmaceutical composition of claim 1, wherein the pH adjusting agent is at least one selected from the group consisting of citric acid, fumaric acid, succinic acid, adipic acid, aspartic acid, glutamic acid, maleic acid, lactic acid, tartaric acid, phosphoric acid, hydrochloric acid, and acetic acid.

5. A method for treating Fontan disease and pulmonary hypertension or erectile dysfunction related to Fontan disease, the method comprising:

administering to a mammal in need thereof a therapeutically effective amount of the pharmaceutical composition of claim 1.

* * * * *